United States Patent [19]

Bredeweg et al.

[11] Patent Number: 5,124,042
[45] Date of Patent: Jun. 23, 1992

[54] METHOD FOR THE DETERMINATION OF THE DEGREE OF NEUTRALIZATION OF PHENOL

[75] Inventors: Robert A. Bredeweg; Richard G. Melcher, both of Midland, Mich.

[73] Assignee: The Dow Chemical Company, Midland, Mich.

[21] Appl. No.: 739,277

[22] Filed: Aug. 1, 1991

[51] Int. Cl.$^5$ .................................................. B01D 61/00
[52] U.S. Cl. ...................... 210/651; 210/650; 210/659; 210/909; 436/131; 436/161; 436/178
[58] Field of Search ............... 210/650, 651, 644, 635, 210/638, 198.2, 909, 459, 456, 659; 436/131, 140, 161, 178

[56] References Cited

U.S. PATENT DOCUMENTS

| | | | |
|---|---|---|---|
| 3,617,546 | 11/1971 | Li | 210/638 |
| 4,448,691 | 5/1984 | Davis | 210/656 |
| 4,715,217 | 12/1987 | Coyne et al. | 210/656 |
| 4,775,496 | 10/1988 | Melcher et al. | 210/635 |
| 4,806,245 | 2/1989 | Böddeker | 210/195.2 |
| 4,819,478 | 4/1989 | Melcher et al. | 210/198.2 |
| 4,891,137 | 1/1990 | Nohl et al. | 210/656 |
| 4,913,821 | 4/1990 | Melcher et al. | 210/635 |
| 4,957,620 | 9/1990 | Cussler | 210/635 |

Primary Examiner—Robert A. Dawson
Assistant Examiner—Ana Fortuna
Attorney, Agent, or Firm—Timothy S. Stevens

[57] ABSTRACT

A three step flow injection analysis method for determining the degree of neutralization of phenol in solution. The first step is to flow a stream of a carrier liquid, such as water, along one side of a two sided semipermeable membrane, such as a silicone rubber membrane. The second step is to flow a stream of water along the other side of the membrane to a detector, such as a flow through ultraviolet spectrometer, the detector being responsive to the concentration of the phenol in the flowing stream of water. The third step is to add a volume of the solution to the flowing stream of carrier liquid so that the solution is carried to the first side of the membrane where a portion of the phenol permeates across the membrane into the flowing stream of water to be detected by the detector, the degree of neutralization of the phenol in the solution being a function of the response of the detector. The results of the method are substantially unaffected by variations in the concentration of the phenol.

4 Claims, 2 Drawing Sheets

METHOD FOR THE DETERMINATION OF THE DEGREE OF NEUTRALIZATION OF PHENOL

BACKGROUND OF THE INVENTION

The classical chemical analysis method for the determination of the degree of neutralization of a known concentration of an acid in solution is to titrate the solution with a base. The endpoint of the classical titration is progressively less distinct as the $pK_a$ of the acid is larger. If the $pK_a$ of the acid is larger than about 8, then the classical titration method becomes difficult. D. Skoog & D. West, *Fundamentals of Analytical Chemistry*, Chapter 14 (1963). The $pK_a$ of phenol is about 10.

Membranes have been widely used in chemical analysis methods. Cortes and Davis, U.S. Pat. No. 4,529,521, used membranes to determine components of interest in latex serum. Stevens, Jewett and Bredeweg, U.S. Pat. No. 4,751,004 used membranes to suppress an Ion Chromatography eluent. Morabito, Melcher, Hiller and McCabe, U.S. Pat. No. 4,962,042, used membranes in a Gas Chromatography system. Stevens, Frawley, Swart, Harris, Diedering, Nicholson and Rothman, U.S. Pat. No. 4,837,161, used membranes to add reagent to a Flow Injection Analysis carrier stream. Melcher and Burt, U.S. Pat. No. 4,913,821, used membranes in a phenol analyzer. Melcher and Cortes, U.S. Pat. No. 4,775,476, used membranes in a Liquid Chromatography system. It is known that the protonated form of an organic acid will permeate across a silicone rubber membrane at a faster rate than the ionized form of the acid.

SUMMARY OF THE INVENTION

A flow injection analysis method for determining the degree of neutralization of phenol in solution. The method comprises three steps. The first step is to flow a stream of carrier liquid along one side of a two sided semipermeable membrane. The second step is to flow a stream of water along the other side of the membrane to a detector, the detector being responsive to the concentration of the phenol in the flowing stream of water. The third step is to add a volume of the solution to the flowing stream of carrier liquid so that the solution is carried to the first side of the membrane where a portion of the phenol permeates across the membrane into the flowing stream of water to be detected by the detector, the degree of neutralization being a function of the response of the detector.

DETAILED DESCRIPTION OF THE INVENTION

Figure 1:
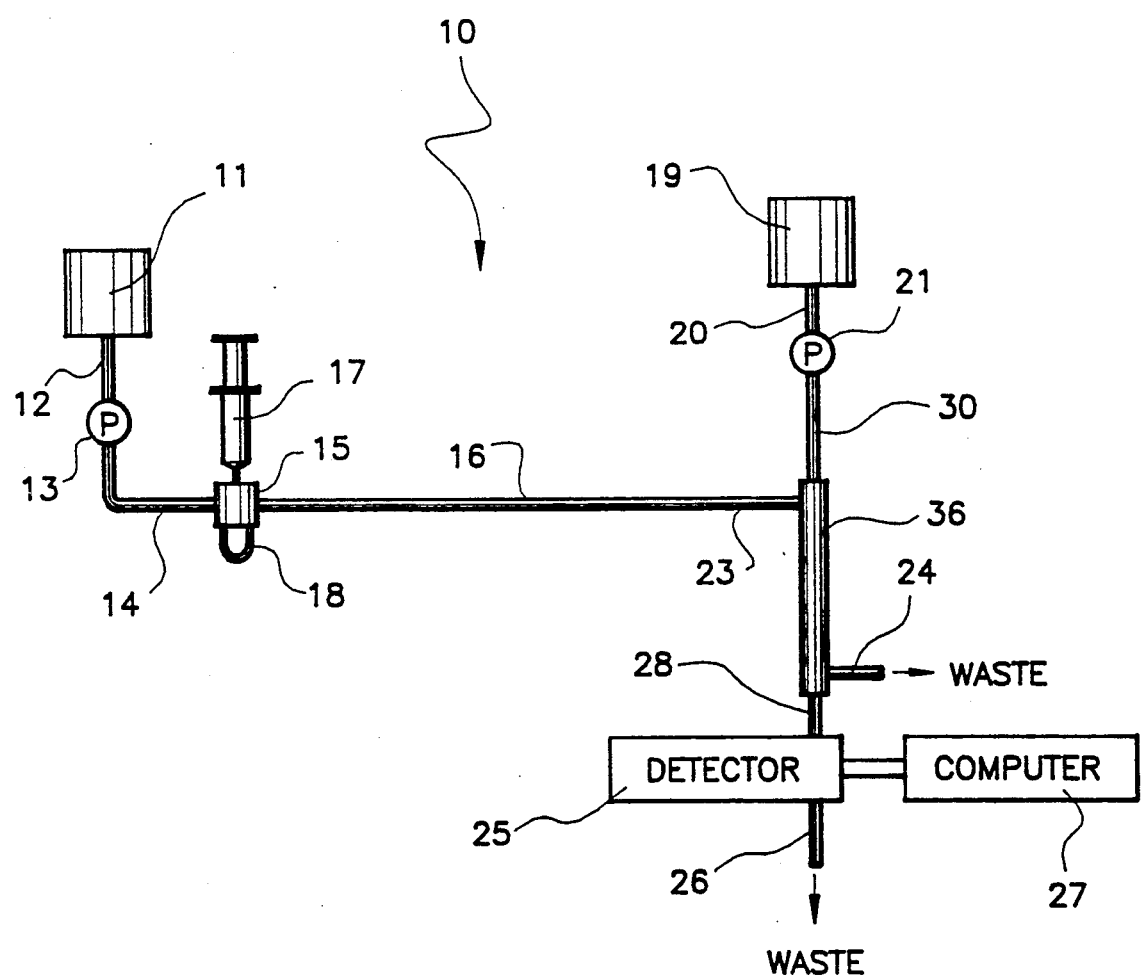
FIG. 1 is a side view, partly in full and partly schematic, of an apparatus for carrying out the method of the present invention, the apparatus including a membrane cell.

Referring now to FIG. 1, therein is shown an apparatus 10 for carrying out the method of the present invention. A reservoir 11 is used to contain a liquid carrier. The liquid carrier is conducted by a tube 12 to a pump 13. Then, the liquid carrier is pumped by the pump 13, e.g., at a flow rate of one milliliter per minute, through the following elements: a tube 14; a loop-type sample injection valve 15; a tube 16; a tube 23; a membrane cell 36; a tube 24; and finally to waste. A liquid sample containing phenol in solution is contained in a syringe 17. The syringe 17 is used to fill a sample loop 18 with the sample. The sample loop 18 has a predetermined volume depending on its length and internal diameter. For example, the loop 18 can contain about one hundred and twenty five microliters. When the valve 15 is actuated, then the sample contained within the loop 18 is added to the flowing stream of liquid carrier flowing in the tube 16 and through the cell 36. A loop-type sample injection valve, as is well known in the art of liquid chromatography, e.g., the Rheodyne Model 7020 sample injection valve available from the Anspec Company, Ann Arbor, MI, is preferred in the present invention. However the use of such a valve is not critical and any means can be used in the present invention to add a volume of the phenol solution to the flowing stream of carrier such as a slider injection valve, a cavity injection valve, a metering rod injection valve (such as the well known Bendix valve, now available from Process Analytics Combustion Engineering Company, Lewisburg, WV, as Model 35267491-2-1 or the Mess Und Apparatetechnik valve Model 101-280, Munchen, Germany) and a sample injected via a syringe and septum as is often done in gas chromatography. The valve 15 can be automatically actuated and sample can be conducted to it directly from a chemical process in an on-line analysis system. The specific liquid carrier used is not critical but it should, of course, be miscible with the sample. Water is a preferred liquid carrier in many applications.

A reservoir 19 is used to contain water. The water contained in the reservoir 19 is conducted to a pump 21 by a tube 20. The pumps 13 and 21 are preferably metering pumps such as the Eldex Model AA pump, available from the Anspec Company as catalog number F1076. The water is pumped by the pump 21, e.g., at a flow rate of four hundred microliters per minute, through the following elements: a tube 30; the membrane cell 36; a tube 28; a flow-through detector 25; a tube 26; and finally to waste.

Figure 2:
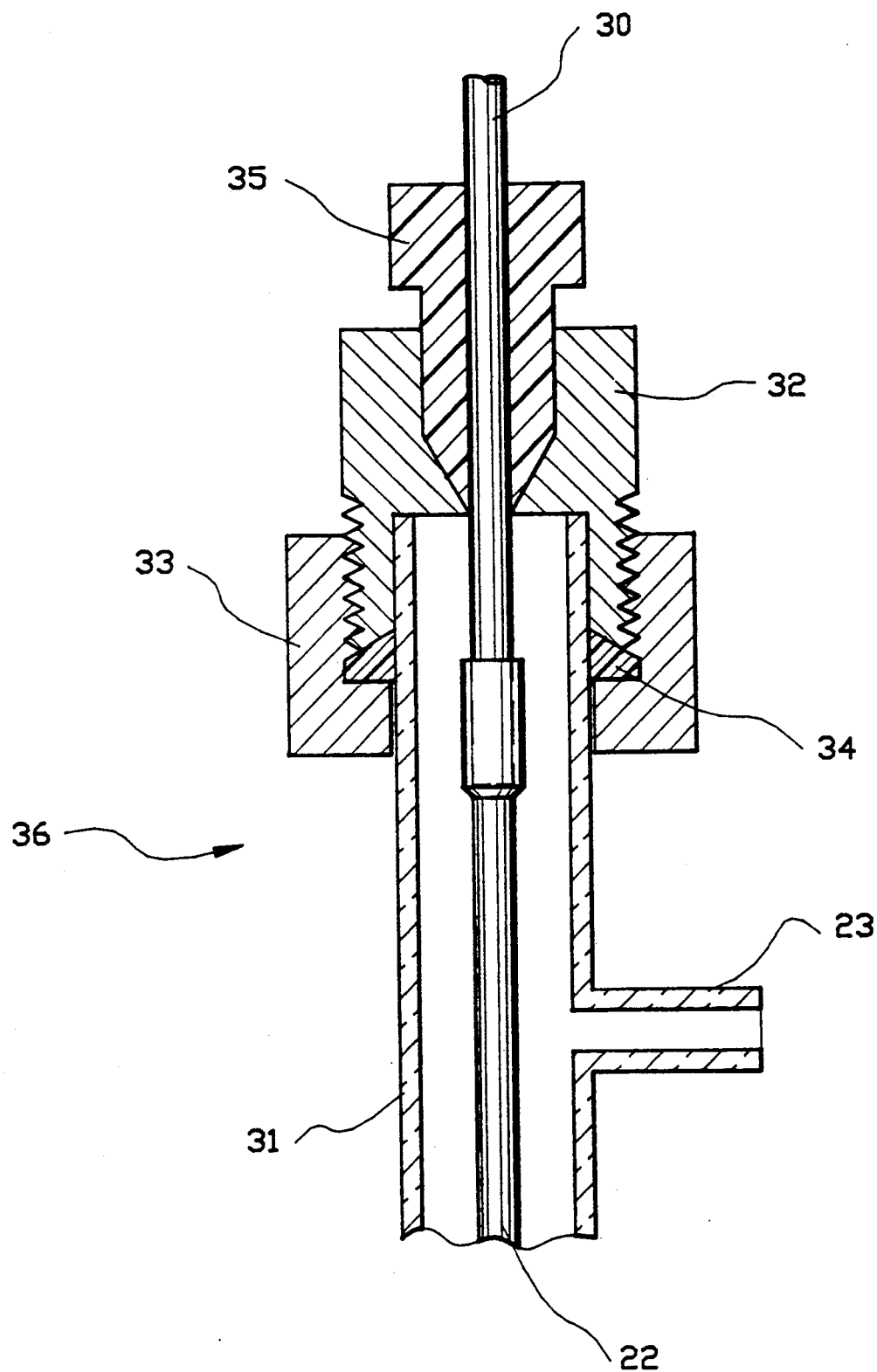
FIG. 2 is a side cross-sectional view of one end of a preferred membrane cell for use in the apparatus shown in FIG. 1.

Referring now to FIG. 2, therein is shown a cross-sectional view of one end of the membrane cell 36. The membrane cell 36 shown in FIG. 2 is highly preferred. The cell 36 has a one quarter inch outside diameter, two millimeter inside diameter, glass shell 31. The tube 23 also referring now to FIG. 1, is connected to the shell 31. A standard one quarter inch liquid chromatography end fitting 32, e.g., the Anspec Company column end fitting H6317, is attached to the shell 31 by a TEFLON ferrule 34, e.g., the Anspec Company TEFLON ferrule catalog number A1567, and a one quarter inch tubing nut 33, e.g., the Anspec Company nut catalog number A1426. The tube 30 is one sixteenth inch outside diameter stainless steel tubing and is positioned through a FINGERTIGHT brand fitting 35 available from the Anspec Company as catalog number H1268. The end of a tubular membrane 22 is stretched over the end of the tube 30 as shown. The membrane 22 is preferably a length of SILASTIC brand silicone rubber medical tubing from the Dow Corning Corporation of Midland Michigan, e.g., a twenty centimeter length of twenty thousandth inch internal diameter, thirty seven thousandth inch outside diameter SILASTIC brand tubing. It is helpful to swell the SILASTIC brand tubing in xylene when stretching it over the end of the tubing 30. When the xylene evaporates, then the membrane 22 shrinks back toward its original dimensions and forms a tight seal to the tube 30. Although silicone rubber is a preferable material for the membrane of the present invention, the membrane can be made of other materials such as other rubbers or polymers as long as the membrane is a semipermeable membrane, i.e., as long as the membrane is more permeable to the unionized form of phenol than it is permeable to the ionized form of phenol. The use of a tubular membrane is not critical, e.g., a sheet type membrane can be used in a suitable membrane cell wherein the membrane partitions the carrier flow from the water flow. The other end of the cell 36 is substantially identical to the end shown in FIG. 2. Therefore, when the fitting 35 is loosened, the tube 30 can be adjusted axially to take up any slack in the membrane 22 and then the fitting 35 can be tightened. The membrane 22 is a two sided membrane. In the apparatus shown, the first side of the membrane 22 is its outside surface or the surface which is exposed to the shell 31 and the second side of the membrane 22 is its inside or bore surface.

Referring now again to FIGS. 1 and 2, the water contained in the reservoir 19 is pumped by the pump 21: through the tube 30; through the inside or bore of the membrane 22; through the tube 28; through the detector 25; and then through the tube 26 to waste. The carrier liquid contained in the reservoir 11 is pumped by the pump 13: through the tube 14; through the valve 15; through the tube 16; along the outside of the membrane 22; and then through the tube 24 to waste. When the valve 15 is actuated, then a predetermined volume of sample solution containing phenol is added to the flowing stream of liquid carrier and is carried to and along the outside of the membrane 22. A portion of the phenol contained therein permeates across the membrane 22 into the flowing stream of water and is conducted to the detector 25 by the tube 28. The detector 25 must be responsive to the concentration of the phenol in the flowing stream of water. A preferred detector 25 is a flow-through ultraviolet spectrometer such as is commonly used as a liquid chromatography detector, e.g., the Kratos SPECTROFLOW 757 variable wavelength detector available from the Anspec Company, supra, as catalog number F2757. A lower cost alternative preferred detector is the LDC/Milton Roy uvMONITOR brand fixed nanometer wavelength detector available from the Anspec Company as catalog number F1096. The degree of neutralization of the phenol is a function of the response of the detector 25 which can be conveniently directed to a computer 27 for data computation and printout, e.g., in the form of a strip chart peak response as well as the peak height, peak area and computed degree of neutralization. A preferred computer 27 is the SpectroPhysics 4270 Chromatography Integrator, Anspec Catalog number F4270. Calibration of the apparatus 10 can be made by injecting standards of a known degree of neutralization.

It is known that the protonated form of an organic acid will permeate across a silicone rubber membrane at a faster rate than the ionized form of the acid. It is further known that as an organic acid is progressively neutralized in solution, then the acid is progressively converted from its unionized form to its ionized form. Thus it would be expected that in the apparatus 10, the response of the detector 25 to an injection of a sample of a partially neutralized organic acid in solution by the valve 15 would be a function of both the concentration and the degree of neutralization of the acid in the sample solution when all other factors, such as the flow rates, temperature and injection size, are held constant. This expectation is generally true when the liquid contained in the reservoir 19 is an organic solvent such as isopropyl alcohol. However, when the liquid contained in the reservoir 19 is water, then the system 10 behaves in an unexpected manner, i.e., the response of the detector 25 is substantially unaffected by variations of the concentration of phenol. For example, the response of the detector 25 is only about seven percent less for a sample containing one percent sodium phenate compared to a sample containing two percent sodium phenate. The term "stream of water" means water or a mixture of water and another material whose presence does not substantially effect the response of the detector to variations in the concentration of phenol in the solution, i.e., no more than a fifteen percent variation of response for a one hundred percent variation in the concentration of phenol. The term "concentration of phenol" means the concentration of both the ionized and unionized forms. Therefore, a primary benefit of the present invention is that the degree of neutralization of phenol in solution can be determined without precisely knowing, having to determine or having to correct for the concentration of phenol in the solution.

Referring now to FIGS. 1 and 2, the flow of liquid carrier is made along the outside of the membrane 22 and the flow of water is made along the inside of the membrane 22. This arrangement, of course, is not critical and the flow of liquid carrier can be made along the inside of the membrane 22 while the flow of water is made along the outside of the membrane 22. In this case, then the first side of the membrane 22 is inside of the membrane 22 and the second side of the membrane 22 is the outside of the membrane 22. It will thus be appreciated that the apparatus shown in FIGS. 1 and 2 is but one of many that could have been used to carry out the method of the present invention. For example, a sheet type membrane cell can be used instead of a tubular type membrane cell as long as the membrane is a semipermeable membrane as define above. Finally, the sensitivity of detection can be increased if the flow of carrier liquid or water or both is temporarily interrupted when the injected phenol solution is carried to the first side of the membrane.

What is claimed is:

1. A flow injection analysis method for determining the degree of neutralization of phenol in a solution, the method being substantially unaffected by variations in the concentration of phenol in the solution, the method comprising the steps of:
    (a) flowing a stream of a carrier liquid along a first side of a semipermeable membrane having the first side and a second side;
    (b) flowing a stream of water along the second side of the membrane to a detector, the detector being responsive to the concentration of phenol in the stream of water;
    (c) adding a volume of the solution to the flowing stream of a carrier liquid so that the solution is carried to the first side of the membrane where a portion of the phenol permeates across the membrane into the flowing stream of water to be detected by the detector, the degree of neutralization being a function of the response of the detector.

2. The method of claim 1, wherein the flow of the stream of a carrier liquid along the first side of the membrane is temporarily interrupted when the solution is carried to the first side of the membrane.

3. The method of claim 1, wherein the flow of water is temporarily interrupted when the solution is carried to the first side of the membrane.

4. The method of claim 1, wherein the flow of the stream of a carrier liquid along the first side of the membrane is temporarily interrupted when the solution is carried to the first side of the membrane and the flow of water is also temporarily interrupted when the solution is carried to the first side of the membrane.

* * * * *